(12) United States Patent
Kim et al.

(10) Patent No.: US 11,672,423 B2
(45) Date of Patent: Jun. 13, 2023

(54) VIBRATION DETECTION APPARATUS

(71) Applicant: Myongji University Industry and Academia Cooperation Foundation, Gyeonggi-Do (KR)

(72) Inventors: Jung Kuk Kim, Gyeonggi-Do (KR); Jae Hyun Park, Gyeonggi-do (KR); Min Kyu Kim, Gyeonggi-Do (KR)

(73) Assignee: Myongji University Industry and Academia Coop Fdn, Gyeonggi-Do (KR)

( * ) Notice: Subject to any disclaimer, the term of this patent is extended or adjusted under 35 U.S.C. 154(b) by 622 days.

(21) Appl. No.: 15/752,313

(22) PCT Filed: Aug. 12, 2016

(86) PCT No.: PCT/KR2016/008866
§ 371 (c)(1),
(2) Date: Apr. 25, 2018

(87) PCT Pub. No.: WO2017/026829
PCT Pub. Date: Feb. 16, 2017

(65) Prior Publication Data
US 2018/0235472 A1    Aug. 23, 2018

(30) Foreign Application Priority Data

Aug. 13, 2015    (KR) .......... 10-2015-0114666

(51) Int. Cl.
*A61B 5/00* (2006.01)
*G01H 17/00* (2006.01)
(Continued)

(52) U.S. Cl.
CPC .......... *A61B 5/0051* (2013.01); *G01H 11/06* (2013.01); *G01H 11/08* (2013.01); *G01H 17/00* (2013.01);
(Continued)

(58) Field of Classification Search
None
See application file for complete search history.

(56) References Cited

U.S. PATENT DOCUMENTS 4,672,976 A * 6/1987 Kroll ................... A61B 5/6831
381/364
4,805,633 A * 2/1989 Kotani .................. A61B 5/11
381/67
(Continued)

FOREIGN PATENT DOCUMENTS

JP    63-137819    9/1988
JP    10-062235    3/1998
(Continued)

OTHER PUBLICATIONS

International Search Report of PCT/KR2016/008866 dated Nov. 16, 2016.

*Primary Examiner* — Benjamin S Melhus
(74) *Attorney, Agent, or Firm* — United One Law Group LLC; Sik Kim; Jhongwoo Peck

(57) ABSTRACT

A vibration detection apparatus is disclosed. The vibration detection apparatus comprises a body configured to have internal space, and a vibration sensor formed on the body and configured to sense vibration from a measuring object. Here, a space exists between the vibration sensor and a surface opposed to the vibration sensor of the body.

9 Claims, 4 Drawing Sheets

(51) Int. Cl.
  *G01H 11/06* (2006.01)
  *G01H 11/08* (2006.01)
  *A61B 5/11* (2006.01)
  *G01H 3/06* (2006.01)
  *A61B 5/25* (2021.01)

(52) U.S. Cl.
  CPC ............. *A61B 5/002* (2013.01); *A61B 5/1102* (2013.01); *A61B 5/25* (2021.01); *A61B 2560/0242* (2013.01); *A61B 2562/0204* (2013.01); *A61B 2562/0217* (2017.08); *G01H 3/06* (2013.01)

(56) References Cited

U.S. PATENT DOCUMENTS

| | | | | |
|---|---|---|---|---|
| 4,840,183 | A * | 6/1989 | Takahashi | A61B 5/11 381/177 |
| 4,947,859 | A * | 8/1990 | Brewer | A61B 7/04 381/355 |
| 5,339,290 | A * | 8/1994 | Greenstein | H04R 17/005 310/800 |
| 5,365,937 | A * | 11/1994 | Reeves | A61B 7/003 600/528 |
| 5,598,845 | A * | 2/1997 | Chandraratna | A61B 8/08 600/459 |
| 5,807,268 | A * | 9/1998 | Reeves | A61B 7/003 600/513 |
| 5,885,222 | A * | 3/1999 | Kassal | A61B 7/04 600/528 |
| 6,438,238 | B1 * | 8/2002 | Callahan | A61B 5/6843 D24/134 |
| 6,988,993 | B2 * | 1/2006 | Sullivan | A61B 7/04 600/528 |
| 8,024,974 | B2 * | 9/2011 | Bharti | H04R 1/46 73/591 |
| 8,771,204 | B2 * | 7/2014 | Telfort | A61B 7/003 600/528 |
| 9,456,801 | B2 * | 10/2016 | Nakamura | A61B 8/13 |
| 10,631,786 | B2 * | 4/2020 | Horii | A61B 7/04 |
| 10,828,007 | B1 * | 11/2020 | Telfort | A61B 5/0205 |
| 2004/0215094 | A1 * | 10/2004 | Baumer | A61B 7/04 600/528 |
| 2005/0200242 | A1 * | 9/2005 | Degertekin | B06B 1/0292 310/334 |
| 2006/0047215 | A1 * | 3/2006 | Newman | A61B 5/282 600/528 |
| 2006/0129067 | A1 * | 6/2006 | Grajales | A61B 5/6804 600/586 |
| 2007/0113649 | A1 * | 5/2007 | Bharti | A61B 5/6814 73/431 |
| 2007/0113654 | A1 * | 5/2007 | Carim | A61B 7/04 73/578 |
| 2009/0175478 | A1 * | 7/2009 | Nakajima | H04R 1/46 381/361 |
| 2011/0301503 | A1 * | 12/2011 | Carim | G01N 29/46 600/586 |
| 2012/0230523 | A1 * | 9/2012 | Ehrlund | H04R 19/04 381/174 |
| 2018/0020931 | A1 * | 1/2018 | Shusterman | A61B 5/02125 600/483 |

FOREIGN PATENT DOCUMENTS

| | | |
|---|---|---|
| JP | 11-266498 | 9/1999 |
| KR | 20-1991-0000663 | 2/1991 |
| WO | 94/05207 A1 | 3/1994 |

* cited by examiner (a)       (b)

(a)       (b)

(a)       (b)

(a)

(b)

VIBRATION DETECTION APPARATUS

PRIORITY

This application claims priority under 35 U.S.C. § 119(a) to a Korean patent application filed on Aug. 13, 2015 in the Korean Intellectual Property Office and assigned Serial No. 10-2015-0114666 and a pct application PCT/KR2016/008866 filed on Aug. 2, 2016, the entire disclosure of which is incorporated herein by reference.

BACKGROUND

Field of the Invention

The present disclosure relates generally to a vibration detection apparatus.

Description of the Related Art

In medical field, an electric signal such as potential or impedance or a vibration signal used for a sphygmomanometer, a stethoscope, a spirometer, etc. has widely been used for diagnosing movement of organs such as miocardia, etc. In respiratory measurement, a technique for measuring temperature change of inhalation and exhalation using a temperature sensor mounted to an end of a nose or a technique for measuring volume change using an instrument having a string shape tied to a chest has been used. Recently, a respiration monitoring technique using an acceleration sensor has been developed. However, the respiration monitoring technique using the acceleration sensor has been restrictively used because its usefulness is low, except special case for requiring very exquisite measurement. Physiologic mechanism related to a ballistocardiography (BCG) for measuring intensity of dynamic movement of a heart, developed by Isaac Stan on 1936, is not known definitely, and the BCG has been limitedly used up to now due to availability and popularity of an ECG, but usage of the BCG has recently increased because a sensor technique is improved. Various sensors such as an acceleration sensor, a strain gauge, etc. are used in the event of measuring medical bio-vibration. However, related instrument and a measuring process are complicated, cost is high, and it is usually difficult to adhere the sensor to a human body because of its surface curvature. Specially, the need for a low-priced disposable biomedical vibration sensor is on the rise due to the possibility of disease transmission or infection and so on.

In a construction field and a civil engineering field, it is becoming a more important issue to predict collapse of a building, a tunnel and a bridge or landslide, etc lately. For the prediction, it is necessary to examine each structure and their surrounding directly using structural mechanics. However, it is difficult to apply the prediction technique to every structure due to human resources requirement and high cost. Hence, collapse prevention facilities are built for most cases in recent years, but there are much difficulties because frequent spot checks are necessary. Since the collapse of structure or building or the landslide goes with physical vibration, the importance of availability of a low-priced vibration sensor applicable efficiently at desired locations is increasing.

In a living noise field, apartment floor noise or vehicle noise on a road, etc. becomes a social problem in recent years. However, a simple technique for solving the problem does not exist. Additionally, a system capable of measuring noise level is expensive. Hence, an apparatus for measuring noise and vibration easily at home and applying the measured result for improvement of the living noise and vibration environment is needed.

Accordingly, a low-priced vibration detection apparatus usable easily in various fields is required.

SUMMARY

The present invention describes a low-priced disposable or semi-permanent vibration sensor that can be applied for vibration detection in various fields, and a vibration detection apparatus equipped with the vibration sensor.

In one aspect, a vibration detection apparatus is disclosed.

A vibration detection apparatus according to one embodiment of the invention comprises a body configured to have internal space; and a vibration sensor formed on the body and configured to sense vibration from a measuring object. Here, a space exists between the vibration sensor and a surface opposed to the vibration sensor of the body.

The vibration sensor is a PVDF sensor.

The vibration detection apparatus further comprises a signal line connected to the vibration sensor to output a sensing signal sensed by the vibration sensor to outside; and an external connecting unit configured to connect electrically the signal line to an external device. Here, the signal line is connected to the external connecting unit through the body.

The vibration detection apparatus further comprises a fixing member formed on a border of a surface on which the vibration sensor is formed and fixed to the measuring object.

The fixing member is an adhesive tape formed along an outer surface of the vibration sensor.

The fixing member is formed along an outer side of the vibration sensor, and is a support fixture extended outside by a constant length in a parallel to a surface on which the vibration sensor is formed.

The internal space of the body is vacuum state or is filled with at least one of air, liquid or gel, and thus internal pressure is adjustable and so a signal filtered in desired frequency is detected.

The body is made up of soft material when the measuring object is curved or soft like a human body, and is made up of hard material in the event of blocking interference influence by vibration except the vibration by the measuring object.

The vibration detection apparatus further comprises an object configured to cover partial central part of a surface of which the vibration sensor is contact with the measuring object. Here, the object amplifies vibration generated from the measuring object.

The object is made up of hard or flexible material, and amplification of the vibration depends on thickness or flexibility of the object.

The vibration detection apparatus further comprises an elastic element located between the vibration sensor and a bottom of the body in the internal space of the body. Here, the elastic element supports the vibration sensor, selects or expands a frequency band of a detectable vibration signal and protects the vibration sensor from strong vibration.

The vibration detection apparatus further comprises the object and the elastic element.

The vibration detection apparatus further comprises an elastic element and a weight sensor located between the vibration sensor and a bottom of the body in the internal space of the body. Here, the elastic element and the weight sensor are formed in a body.

The vibration detection apparatus further comprises the object, the elastic element and the weight sensor.

The vibration detection apparatus further comprises an electrolyte gel formed from an upper part of the vibration sensor to a bottom of the internal space of the body; and an electrode for bioelectrical signal measurement connected to the electrolyte gel and projected outside of the body.

In another aspect, a vibration detection device is disclosed.

A vibration detection apparatus according to another embodiment of the invention comprises a body; a vibration sensor formed on a surface of the body and configured to sense vibration from a measuring object; an electronic device connected to other surface of the body; and a signal line configured to transmit a sensing signal sensed by the vibration sensor to the electronic device. Here, the signal line is connected electrically to the electronic device through the body.

The electronic device is formed as a single unit with the body.

The vibration detection apparatus further comprises an external connecting unit configured to connect the signal line to the electronic device. Here, the electronic device is connected to the external connecting device and includes a detachable connector connected to the external connecting device.

The vibration detection apparatus further comprises an external connecting unit connected to the signal line; and a wire connector connected to the external connecting unit and includes a signal line extended outside in order to connect a detachable connector combined with the external connecting unit to the electronic device.

The electronic device processes a detection signal outputted from the vibration sensor and transmits the processed result to an external device through a wire or wireless communication.

DETAILED DESCRIPTION

Example embodiments of the invention are disclosed herein. However, specific structural and functional details disclosed herein are merely representative for purposes of describing example embodiments of the invention, however, example embodiments of the invention may be embodied in many alternate forms and should not be construed as limited to example embodiments of the invention set forth herein.

In describing the invention, if it is determined that explanation about relevant published technique blurs important point of the invention, any description about the technique will be omitted. Furthermore, numbers used in the invention are discernment sign for discriminating one element from another element.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

Hereinafter, various embodiments of the invention will be described in detail with reference to accompanying drawings. Like numbers refer to like elements throughout the description of the figures.

Figure 1:
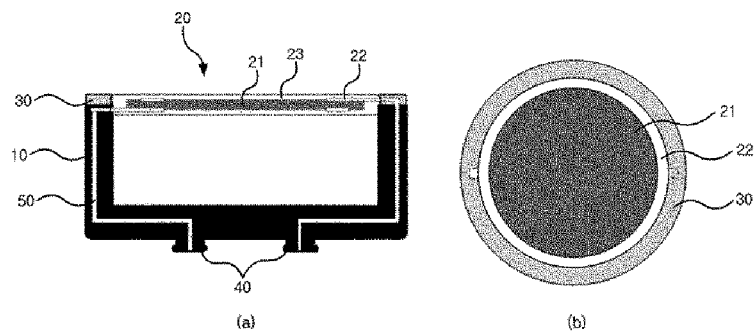
FIG. 1 is a view illustrating a structure of a vibration detection apparatus according to one embodiment of the invention.

FIG. 1 is a view illustrating a structure of a vibration detection apparatus according to one embodiment of the invention. Particularly, (a) in FIG. 1 is a sectional side view illustrating the vibration detection apparatus, and (b) in FIG. 1 is a top view illustrating the vibration detection apparatus.

In FIG. 1, the vibration detection apparatus includes a body 10, a vibration sensor, e.g. Polyvinylidene fluoride PVDF sensor 20, a fixing member 30, an external connecting unit 40 and a signal line 50. Hereinafter, it is assumed that the vibration sensor is the PVDF sensor 20, for convenience of description.

The body 10 is formed in a can shape inside which is empty. For example, internal space is state of vacuum or filled with air, liquid, gel, etc. As a result, internal pressure of the body 10 may be adjusted to filter only desired frequency, and thus a signal corresponding to the filtering can be detected. Additionally, a PVDF sensor film may be protected from strong vibration. Furthermore, the internal space of the body 10 may block external vibration, reduce outside effect, enhance sensitivity of the PVDF sensor 20, or protect the PVDF sensor 20.

For example, the body 10 may have cylindrical shape when its top has circular shape, as shown in (b) in FIG. 1. The top of the body 10 may have elliptical shape, a triangular shape, a rectangular shape, or other polygonal shape, etc., which is shown in FIG. 7.

Figure 7:
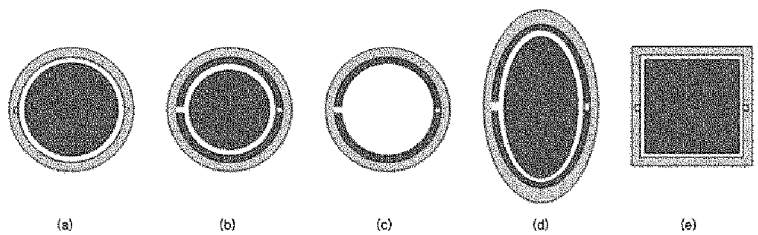
FIG. 7 is a view illustrating various shapes of the vibration detection apparatus.

FIG. 7 is a view illustrating various shapes of the vibration detection apparatus. Particularly, FIG. 7 shows the top of the vibration detection apparatus including the PVDF sensor 20 and the fixing member 30. In FIG. 7, the top of the vibration detection apparatus has circular shape in (a) to (c), and (b) and (c) illustrate an area and arrangement of an electrode 22 adjusted based on the shape in (a). (d) in FIG. 7 shows a top of the vibration detection apparatus with elliptical shape, and (e) in FIG. 7 illustrates a top of the vibration detection apparatus having rectangular shape.

The body 10 may be made up of hard or soft material. For example, the body 10 may be made up of soft material when a measuring object is curved or soft such as a human body. The body 10 may be made up of hard material in the event of blocking interference influence by vibration except the vibration by the measuring object.

The PVDF sensor 20 is formed on the top of the body 10, and includes a PVDF film 21, two electrodes 22 adhered to both sides of the PVDF film 21 and two protection films 23 covering the two electrodes 22.

That is, the top of the body 10 on which the PVDF sensor 20 is formed is contacted with the measuring object.

The PVDF sensor 20 has generally a feature of outputting an electrical signal in proportion to intensity change of applied vibration because it has a feature of a piezoelectric element. Moreover, detection sensitivity and detection characteristics of the vibration of the PVDF sensor 20 may be adjusted depending on amount of polymer material coated on the PVDF film 21, a shape of the electrode 22 of the PVDF sensor 20, or thickness of the protection film 23, etc.

Figure 8:
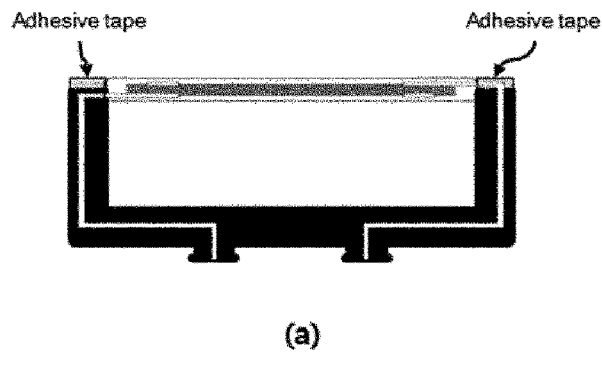
FIG. 8 is a view illustrating type of the fixing member according to one embodiment of the invention.
Figure 8:
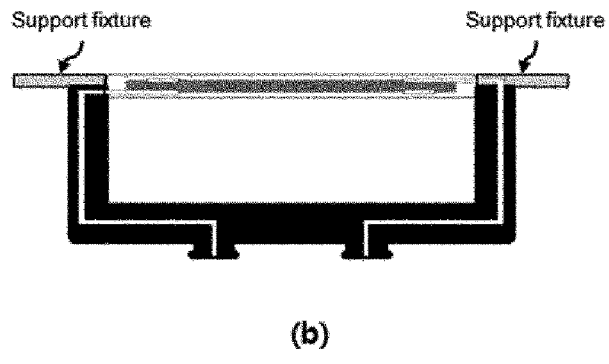

The fixing member 30 is formed on a border of the top, and fixes the vibration detection apparatus to the measuring object. For example, FIG. 8 is a view illustrating type of the fixing member 30 according to one embodiment of the invention. (a) In FIG. 8 shows a case that the fixing member 30 is an adhesive tape, and (b) in FIG. 8 illustrates a case that the fixing member 30 is a support fixture.

In the event that the fixing member 20 is the adhesive tape, the adhesive tape may be formed along the border of the top (upper part) of the body 10, i.e. an outer part of the PVDF sensor 20. The adhesive tape may be used as the fixing member 30 when the measuring object can be adhered by the adhesive tape like a human body.

In the event that the support fixture is used as the fixing member 30 as shown in (b) in FIG. 8, the support fixture may be formed along the border of the top of the body 10, i.e. the outer part of the PVDF sensor 20. The support fixture may be extendedly formed outside by a constant length in a parallel to an upper surface of the body 10, in order to fix the support fixture to the measuring object using a screw or a nail, etc. A hole into which the screw or the nail, etc. is inserted may be formed on an extended part. In the event that the measuring object can't be adhered by the adhesive tape like a structure, the support fixture may be used as the fixing member 30.

The external connecting unit 40 is formed on the other side of the body 10, and connects the two electrodes 22 of the PVDF sensor 20 to an external device. For example, two external connecting units 40 corresponding to the two electrodes 22 may be formed on a lower side of the body 10 as one body with the body 10, and their shapes may be preset according to type of the external device.

The signal line 50 connects the two electrodes 22 of the PVDF sensor 20 to the external connecting unit 40. For example, the signal line 50 may be formed as one body with the body 10 by being buried in the body 10 when the body 10 is manufactured.

FIG. 2 to FIG. 6 are views illustrating a vibration detection apparatus according to another embodiment of the invention. Hereinafter, any description concerning the same elements as in FIG. 1 will be omitted.

Figure 2:
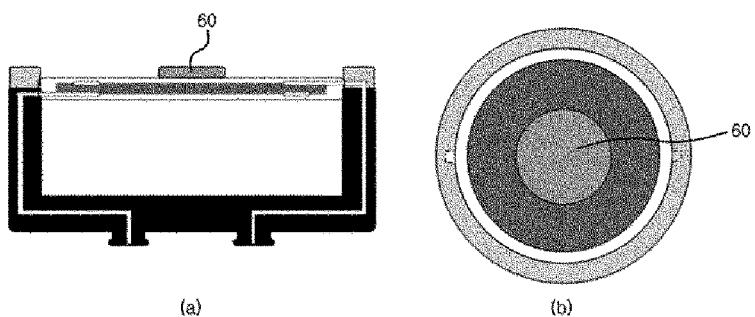
FIG. 2 to FIG. 6 are views illustrating a vibration detection apparatus according to another embodiment of the invention.

In FIG. 2, the vibration detection apparatus may include an object 60 for covering partial central part of the top of the PVDF sensor 20. For example, the object 60 may be made up of hard material of which shape is not easily changed or flexible material, and may amplify intensity of vibration so that the PVDF sensor 20 can measure precisely intensity of vibration generated from the measuring object. Intensity amplification degree of the vibration depends on thickness and flexibility of the object 60. A hard object 60 may be applied when the intensity of the vibration generated from the measuring object is weak. That is, the PVDF sensor 20 may detect more sensitively the vibration at a part on which the object 60 exists.

Figure 3:
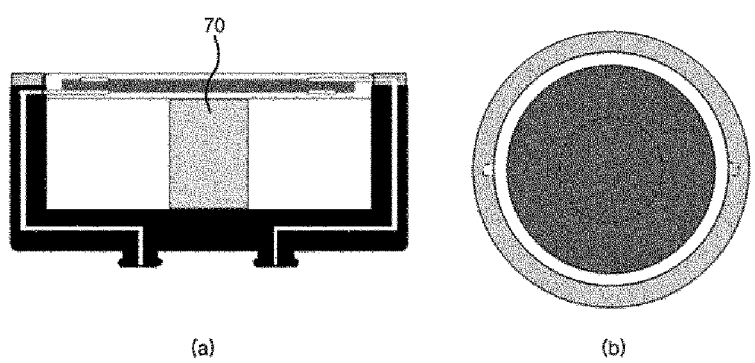

Referring to FIG. 3, a vibration detection apparatus may further include an elastic element 70 located between a central lower part of the PVDF sensor 20 and a bottom of the body 10, in the internal space of the body 10. Here, the elastic element 70 may support the PVDF sensor 20, and reduce cutoff frequency of the PVDF sensor 20 having differentiator feature. That is, the elastic element 70 may be used for selecting or expanding a frequency band where a vibration signal is detectable. Additionally, the elastic element 70 may protect the PVDF sensor 20 from strong vibration.

Figure 4:
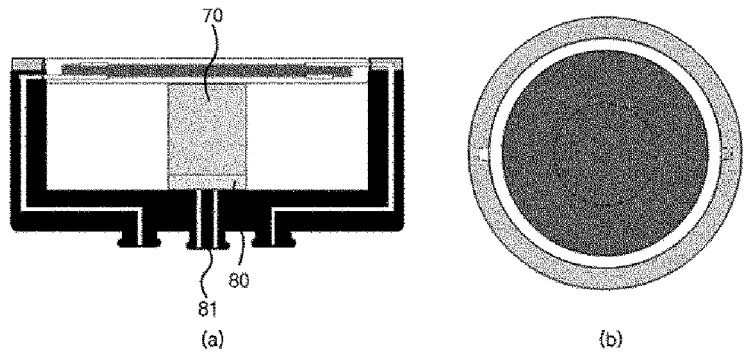

In FIG. 4, a vibration detection apparatus may include further an electric element 70 located between the central lower part of the PVDF sensor 20 and the bottom of the body 10 and a weight sensor 80, in the internal space of the body 10. Here, the elastic element 70 and the weight sensor 80 are formed in a body. Hence, the vibration detection apparatus may measure further pressure of the vibration through the weight sensor 80. For example, the weight sensor 80 may be adhered to the bottom of the body 10, and the elastic element 70 may be adhesively inserted between an upper part of the weight sensor 80 and the central lower part of the PVDF sensor 20. Here, the weight sensor 80 may become a load cell, and the vibration detection apparatus may have a structure that the load cell is added to a lower part of the elastic element 70 in FIG. 3.

Since the vibration detection apparatus includes further the weight sensor 80, the vibration detection apparatus may include further additional external connecting unit 81 for connecting a signal line of the weight sensor 80 to an external device, like the external connecting unit 40.

Figure 5:
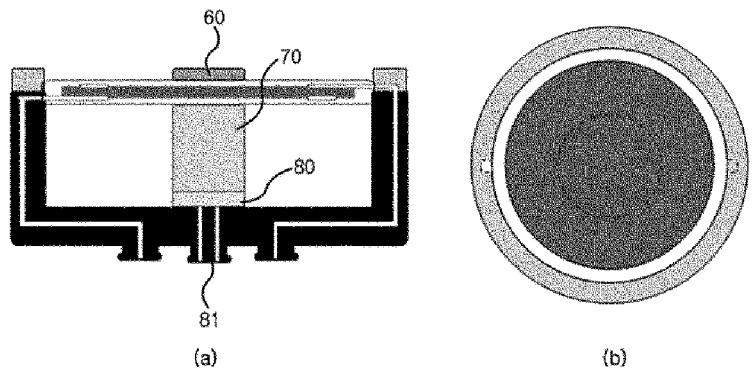

In FIG. 5, a vibration detection apparatus may include further a hard object 60 for covering a central part of the upper part of the PVDF sensor 20 and an elastic element 70 located between the central lower part of the PVDF sensor 20 and the bottom of the body 10 and a weight sensor 80 in the internal space of the body 10. That is, the vibration detection apparatus shown in FIG. 5 has a structure that additional elements in FIG. 2 and FIG. 4 are combined. Accordingly, the vibration detection apparatus in FIG. 5 may have every feature of the additional elements in FIG. 2 to FIG. 4.

Figure 6:
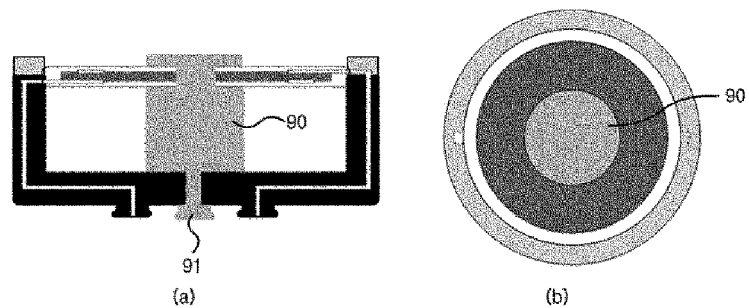

In FIG. 6, the vibration detection unit may include further an electrolyte gel 90 formed from an upper part of the PVDF sensor 20 to the bottom of the body 10 and an electrode 91 for bioelectrical signal measurement which is connected to the electrolyte gel 90 and projected outside the body 10. That is, the vibration detection apparatus in FIG. 6 has a structure that the electrode 91 is added to the vibration detection apparatus in FIG. 1. The vibration detection apparatus may detect an electrical signal as well as a vibration signal generated in the human body.

For example, the vibration detection apparatus in FIG. 6 may have a structure that an ECG electrode is added to the vibration detection apparatus in FIG. 1. That is, the vibration detection apparatus in FIG. 6 may be produced by generating a hole on a center of the PVDF sensor 20 in the vibration detection apparatus in FIG. 1, inserting the electrolyte gel 90 for ECG measurement through the generated hole, and then inserting the electrode 91 for detecting an ECG signal through the body 10 so that the electrode 91 is formed from a lower part of the electrolyte gel 90 to outside of the body 10. The vibration detection apparatus in FIG. 6 may detect simultaneously the vibration signal and the ECG signal, and thus it may be applied to a medical field. The vibration detection apparatus as one device may detect individually or simultaneously various bioelectrical signals such as the ECG signal, a BCG, etc.

Figure 9:
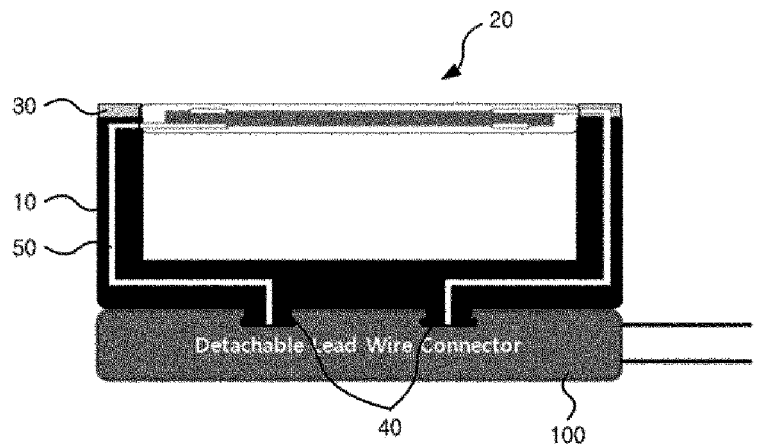
FIG. 9 is a view illustrating a combination of a vibration detection apparatus and a wire connector according to one embodiment of the invention.

FIG. 9 is a view illustrating a combination of a vibration detection apparatus and a wire connector according to one embodiment of the invention.

In FIG. 9, the wire connector 100 may be connected to the external connecting unit 40 of the vibration detection apparatus, and be detachable to the external connecting unit 40. Furthermore, the wire connector 100 may include a signal line extended outside so that it is connected to an external device. Accordingly, the wire connector 100 may connect electrically the vibration detection apparatus to the external device.

Figure 10:
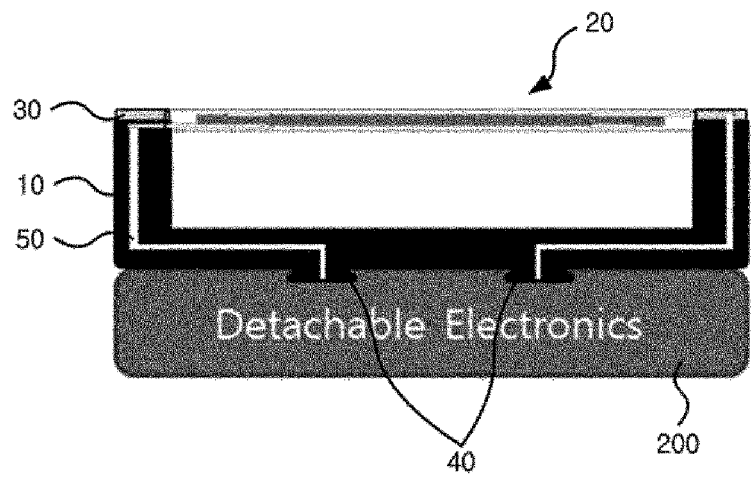
FIG. 10 and FIG. 11 are views illustrating combination of a vibration detection apparatus and a signal processing device according to one embodiment of the invention.
Figure 11:
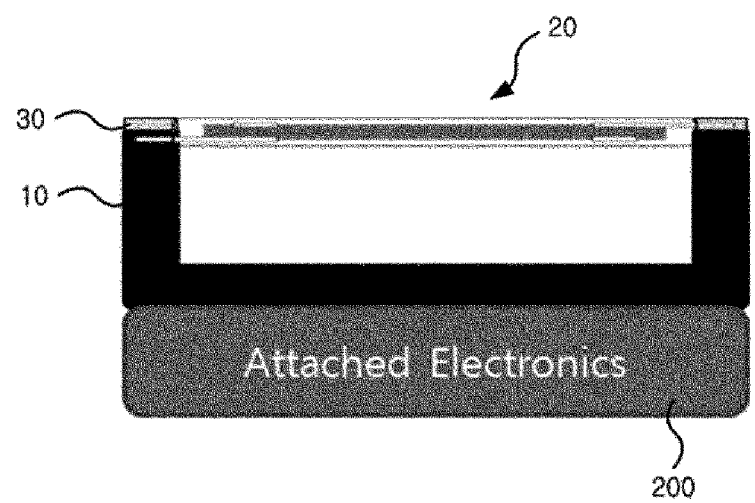

FIG. 10 and FIG. 11 are views illustrating combination of a vibration detection apparatus and a signal processing device according to one embodiment of the invention.

Referring to FIG. 10, the signal processing device 200 may be connected to the external connecting unit 40 of the vibration detection apparatus, and include a detachable connector connected to the external connecting unit 40 for the purpose of the connection.

In FIG. 11, the signal processing device 200 and the vibration detection apparatus may be formed in a body. For example, the elements of the signal processing device 200 are installed in the vibration detection apparatus.

Hereinafter, the signal processing device 200 will be described with reference to a drawing FIG. 12.

Figure 12:
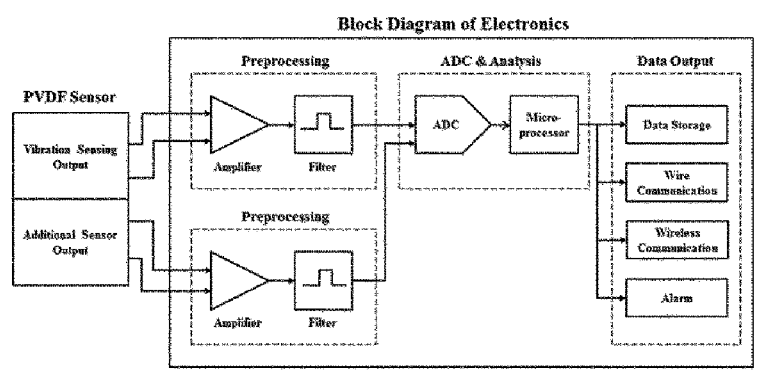
FIG. 12 is a view illustrating schematically the signal processing device connected to the vibration detection apparatus according to one embodiment of the invention.

FIG. 12 is a view illustrating schematically the signal processing device connected to the vibration detection apparatus according to one embodiment of the invention.

In FIG. 12, the signal processing device 200 may include an amplifier and a filter in preprocessing for receiving a signal outputted from the PVDF sensor 20 of the vibration detection apparatus or additional sensor, reducing noise and amplifying the signal, an analog to digital converter ADC for converting a preprocessed analog signal to a digital signal, a microprocessor for performing a signal processing and interpretation by using the digital signal and a wire/wireless output unit (communication unit) for outputting a detection signal outputted from the microprocessor to outside. Moreover, the signal processing device 200 may further include a memory for storing the detection signal or an alarm module for performing an alarm according to the detection signal.

On the other hand, the signal processing device 200 is not limited as the above elements, and element and operation of the signal processing device 200 may depend on a function of corresponding device. However, transmission of the signal to the external device is necessary irrespective of kind of the device, and thus the signal processing device 200 may include necessarily the communication unit.

The embodiments of the invention described above are disclosed only for illustrative purposes. A person having ordinary skill in the art would be able to make various modifications, alterations, and additions without departing from the spirit and scope of the invention, but it is to be appreciated that such modifications, alterations, and additions are encompassed by the scope of claims set forth below.

The vibration detection apparatus of the invention may be easily applied to various fields where vibration detection is necessary, and may be single used only or used semi-permanently.

Specially, the vibration detection apparatus of the invention may be applied to various fields for measurement of a bioelectrical signal, movement detection, collapse prediction or landslide prediction in a construction or a civil engineering, measurement of living noise, etc. In addition, a low-priced small light sensor usable with high sensitivity may be manufactured and supplied, due to the vibration detection apparatus.

What is claimed is:

1. A vibration detection apparatus comprising:
a body including an internal space formed therein;
a vibration sensor formed on one side of the body and configured to sense vibration from a measuring object, wherein the vibration sensor comprises a PVDF film, first and second electrodes adhered to both sides of the PVDF film, and protection films covering the first and second electrodes;
signal lines connected to the vibration sensor, wherein the signal lines are configured to output a sensor signal obtained by the vibration sensor to an external device;
external connectors formed on another side of the body, an electrolyte gel formed in the internal space of the body from an upper surface of the vibration sensor to a bottom of the internal space of the body;
and a third electrode for bioelectrical signal measurement, wherein the third electrode is connected to the electrolyte gel and protrudes outside of the body, wherein the internal space is formed between the vibration sensor and a surface of the body opposite from the vibration sensor,
wherein the signal lines electrically connected to the first and second electrodes are electrically connected to the external device through corresponding external connectors, respectively,
wherein an entirety of the signal lines is embedded within the body without being exposed to the internal space or to an exterior of the vibration detection apparatus,
and wherein the internal space of the body is filled with at least one of liquid and gel configured to allow an internal pressure of the body to be adjusted and configured to allow a signal filtered for a desired frequency to be detected.

2. The vibration detection apparatus of claim 1, further comprising:
a fixing member formed on a periphery of a surface on which the vibration sensor is formed, wherein the fixing member attaches the vibration detection apparatus to the measuring object.

3. The vibration detection apparatus of claim 2, wherein the fixing member is an adhesive tape formed along an outer surface of the vibration sensor.

4. The vibration detection apparatus of claim 2, wherein the fixing member is formed along an outer side of the vibration sensor, and where the fixing member includes a support fixture extended outside of the body by a predetermined length in a direction parallel to the surface on which the vibration sensor is formed.

5. The vibration detection apparatus of claim 1, wherein a rigidity of the body is determined based on a shape or rigidity of the measuring object, and where the rigidity of the body is determined to prevent interference from vibration that is other than the vibration of the measuring object.

6. The vibration detection apparatus of claim 1, further comprising:
a covering member that partially covers a central portion of a surface of the vibration sensor that contacts the measuring object, wherein the covering member is configured to amplify the vibration from the measuring object.

7. The vibration detection apparatus of claim 6, wherein an amplification of the vibration is varied based on a thickness or rigidity of the covering member.

8. The vibration detection apparatus of claim 6, further comprising:
   an elastic element located between the vibration sensor and the bottom of the internal space of the body, wherein the elastic element is configured to support the vibration sensor, adjust a frequency band that is detectable, and protect the vibration sensor from impacts.

9. The vibration detection apparatus of claim 6, further comprising:
   an elastic element and a weight sensor located in the internal space of the body between the vibration sensor and the bottom of the internal space of the body,
   wherein the elastic element and the weight sensor are formed as a single component.

\* \* \* \* \*